(12) United States Patent
Ryan et al.

(10) Patent No.: US 6,827,716 B2
(45) Date of Patent: Dec. 7, 2004

(54) METHOD OF IDENTIFYING AND TREATING A PATHOLOGIC REGION OF AN INTERVERTEBRAL DISC

(75) Inventors: Thomas P. Ryan, Flemington, NJ (US); Martin A. Reynolds, Mansfield, MA (US); Hassan Serhan, South Easton, MA (US)

(73) Assignee: Depuy Spine, Inc., Raynham, MA (US)

( * ) Notice: Subject to any disclaimer, the term of this patent is extended or adjusted under 35 U.S.C. 154(b) by 169 days.

(21) Appl. No.: 10/261,215

(22) Filed: Sep. 30, 2002

(65) Prior Publication Data

US 2004/0064023 A1 Apr. 1, 2004

(51) Int. Cl.[7] ............................................. A61B 18/18
(52) U.S. Cl. ......................... 606/41; 606/27; 607/99; 607/101; 607/116
(58) Field of Search ............................. 606/27–31, 41, 606/48–50; 607/99, 101, 102, 116, 117

(56) References Cited

U.S. PATENT DOCUMENTS

| | | | |
|---|---|---|---|
| 5,941,834 A | 8/1999 | Skladnev et al. | |
| 5,976,076 A | 11/1999 | Kolff et al. | |
| 6,004,262 A | 12/1999 | Putz et al. | |
| 6,015,406 A | 1/2000 | Goble et al. | |
| 6,073,051 A | * | 6/2000 | Sharkey et al. ............... 607/99 |
| 6,095,149 A | 8/2000 | Sharkey et al. | |
| 6,264,650 B1 | 7/2001 | Hovda et al. | |
| 6,277,112 B1 | 8/2001 | Underwood et al. | |
| 6,602,248 B1 | * | 8/2003 | Sharps et al. .................. 606/32 |
| 6,604,003 B2 | * | 8/2003 | Fredricks et al. ............. 607/99 |
| 2003/0069569 A1 | * | 4/2003 | Burdette et al. .............. 606/27 |
| 2003/0158591 A1 | * | 8/2003 | Brett ........................... 607/89 |

FOREIGN PATENT DOCUMENTS

WO  WO 02/28302 A1  4/2002

* cited by examiner

Primary Examiner—Michael Peffley
(74) Attorney, Agent, or Firm—Thomas M. DiMauro

(57) ABSTRACT

This invention relates to a method of treating an intervertebral disc comprising locally identifying a pathologic tissue site and therapeutically treating the identified site.

26 Claims, 5 Drawing Sheets

METHOD OF IDENTIFYING AND TREATING A PATHOLOGIC REGION OF AN INTERVERTEBRAL DISC

BACKGROUND OF THE INVENTION

U.S. Pat. No. 6,277,112, assigned to Arthrocare ("Underwood"), discloses methods for therapeutically applying electrical energy to tissue within a patient's spine, including introducing an active electrode into the patient's spine, positioning an active electrode near a target tissue, and applying a high voltage across the electrode to produce a plasma to volumetrically remove, ablate or coagulate the target tissue.

Underwood also discloses methods for therapeutically treating a patient's knee, and discloses that the insertion of the probe is usually guided by an arthroscope that includes a light source and a video camera to allow the surgeon to selectively visualize a zone within the knee joint. See Underwood at col. 31, lines 6–9.

U.S. Pat. No. 6,264,650, also assigned to Arthrocare ("Hovda"), discloses methods for therapeutically applying electrical energy to tissue within a patient's spine, including introducing an active electrode into the patient's spine, positioning an active electrode near a target tissue, and applying a high voltage across the electrode to produce a plasma to volumetrically remove, ablate or coagulate the target tissue.

Hovda further discloses that "the system may include an endoscope with a fiber optic headlight for viewing the surgical site, and that the endoscope may be intergral with the therapeutic probe or part of a separate instrument. See Hovda at col. 21, lines 22–25. Hovda does not teach how this headlight is used. Hovda appears to distinguish between the surgical site (i.e., the entire disc) and the target site (i.e., the tissue to be treated). Therefore, Hovda does not specifically disclose using the headlight to identify a pathologic region within a target tissue.

In sum, Hovda discloses therapeutic devices and optical devices, but does not teach that the optical device can be used to identity a pathologic region within a target tissue.

U.S. Pat. No. 6,095,149 ("Sharkey") discloses a method of treating interverterbal discs by using a flexible catheter to position a functional element within the disc. Sharkey discloses functional elements including any element capable of aiding diagnosis, delivering energy, or delivering or removing a material from a location adjacent the element's location in the catheter, such as an opening in the catheter for delivery of a fluid or for suction, a thermal energy delivery device (heat source), a mechanical grasping tool for removing or depositing a solid, a cutting tool (which includes all similar operations, such as puncturing), a sensor for measurement of a function (such as electrical resistance, temperature or mechanical strength), or a functional element having a combination of these elements. See Sharkey at col. 14, lines 43–54.

Sharkey further discloses that a variety of different materials can also be delivered to the disc, including electrolyte solutions via the catheter and/or introducer to the disc. Sharkey discloses that the electrolyte solution helps the physician view the disc. See Sharkey at col. 21–22.

Sharkey discloses that the catheter is positionable to selected sites near the annulus fibrosus for the delivery of therapeutic and/or diagnostic agents including but not limited to electromagnetic energy, electrolyte solutions, and contrast media and thermal energy. See Sharkey at col. 15, lines 45–52.

The only elements capable of aiding diagnosis actually specified by Sharkey are contrast agents. These contrast agents are typically detected by fluoroscopy. Sharkey does not disclose diagnostic elements upon the probe that actively detect a pathologic region within a target tissue.

Moreover, although Sharkey discloses diagnostic elements, energy delivery elements, and six other functional elements, and combinations thereof, Sharkey does not disclose the specific combination of a diagnostic element and an energy delivery element, nor an optical diagnostic element.

U.S. Pat. No. 6,015,406 ("Goble") discloses an electrode-containing electrosurgical instrument for treating tissue in the presence of an electrically-conductive fluid ("ECF") medium. Goble discloses that the procedure may be used for thermal shrinkage of joint capsules, for discectomy either in the treatment of disc prolapse or as part of a spinal fusion via a posterior or anterior approach to the spine. Goble at col. 4, lines 52–57. Goble further discloses that the procedures may include simultaneous viewing of the site via an endoscope or using an indirect visualization means. See Goble at col. 5, lines 24–26.

Goble does not teach using the endoscope to identify pathologic tissue.

In sum, conventional methods for therapeutically treating interveterbral discs do not also teach using a probe having an element that actively senses the pathologic region of the disc prior to treatment.

U.S. Pat. No. 5,941,834 ("Skladnev") discloses a probe for identifying different tissue types within body canals such as the endocervical canal. The probe comprises optical and electrode measuring systems disposed on opposite sides of a cylinder, wherein the systems are designed for taking optical and electrical measurements simultaneously on the same area of tissue. Sladnev discloses that probes using optical fibers are temperature sensitive.

Skladnev does not discloses a probe having a therapeutic functional element, nor a probe suitable for entering an intervertebral disc.

U.S. Pat. No. 5,976,076 discloses a stereo laparoscope for producing a stereoscopic optical image of an intracorporal region to be viewed through a small incision. Kolff does not disclose a probe having a therapeutic functional element.

U.S. Pat. No. 6,004,262 ("Putz") discloses a surgical device comprising a probe having a fiber optic strand disposed at its distal end, and electrode wires. In one method of using the device, the "seeing eye" optical strand visually guides the assembly to the epidural space of the spinal column, and the electrode wires either monitor electrical activity at the site or stimulate tissue at the site.

Neither Skladnev, nor Kollf, nor Putz discloses a probe having a therapeutic functional element, nor a probe suitable for entering an intervertebral disc.

SUMMARY OF THE INVENTION

The present invention relates to using a "see and treat" system to better assess and treat a pathologic region within an intervertebral disc. In particular, the present invention relates to a method of treatment comprising a first step wherein a diagnostic element is positioned adjacent or within the disc and provides information to the clinician that allows the clinician to identify a pathologic region of the disc. In a second step, a therapeutic element treats the identified pathologic region.

By improving localization of the pathologic regions with the diagnostic element, the therapy may be more accurately delivered, and so should have a higher chance of success.

Because the present invention provides for localized treatment, the clinician disrupts the target tissue only where necessary, thereby preserving healthy tissue. Because the present invention allows diagnosis and treatment to be coupled, the treatment is done immediately after diagnosis, thereby saving time.

Therefore, in accordance with the present invention, there is provided a method of therapeutically treating an intervertebral disc having a pathologic region, the method comprising the steps of:

a) positioning a probe having a diagnostic element within or adjacent to the disc,
b) activating the diagnostic element to identify the pathologic region, and
c) therapeutically treating the identified pathologic region.

Also in accordance with the present invention, there is provided a method of therapeutically treating an intervertebral disc having a pathologic region, the method comprising the steps of:

a) positioning a probe having a diagnostic element and a therapeutic element within or adjacent to the disc, the diagnostic element comprising a sensor and an active element,
b) transmitting energy through the active element to target tissue to produce a signal from the pathologic region,
c) transmitting the signal through the sensor,
d) evaluating the signal to identify the pathologic region, and
e) therapeutically treating the identified pathologic region.

Also in accordance with the present invention, there is provided a probe for diagnosing and therapeutically treating a pathologic region within an intervertebral disc, comprising:

a) a diagnostic element adapted to identify the pathologic region, and
a therapeutic element adapted to therapeutically treat the pathologic region.

DETAILED DESCRIPTION OF THE INVENTION

Figure 1:
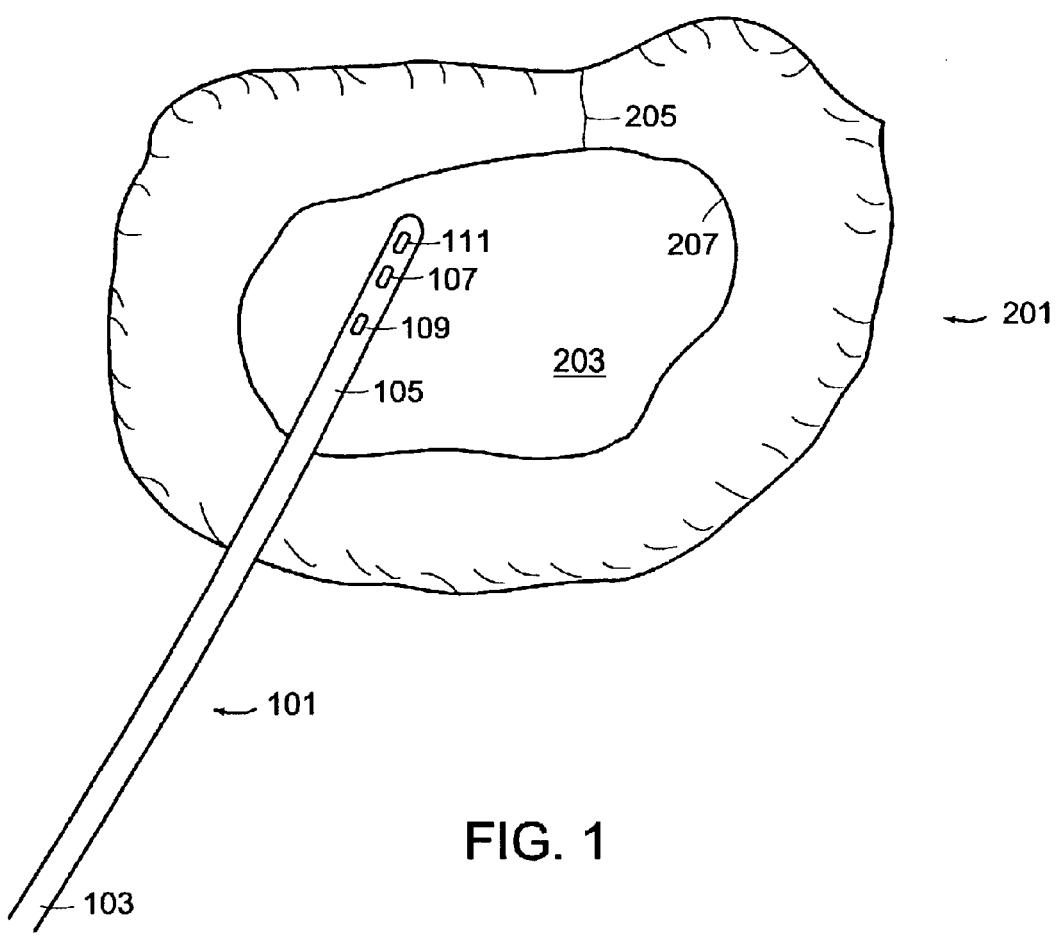
FIGS. 1 and 2 disclose a preferred probe of the present invention within an intervertebral disc.

Without wishing to be tied to a theory, it is believed that damage to or degeneration of the intervertebral disc may contribute to back or leg pain in at least one of the following ways:

a) innervation of its annulus fibrosus component, leading to chemical and mechanical sensitization of the nociceptors contained therein;
b) mechanical instability due to a fissure in its annulus fibrosus component; and
c) herniation of its nucleus pulposus component.

Accordingly, when the intervertebral disc is so selected as the target tissue, the step of therapeutically treating the intervertebral disc may comprise any one of i) coagulating the collagen contained within an annulus fibrosus portion of the disc, ii) denervating the nociceptors contained within an annulus fibrosus portion of the disc, and iii) removing mass from the nucleus pulposus component within the disc, or a combination thereof.

In some preferred embodiments, the device enters the tissue site via a percutaneously placed needle.

In some embodiments, the probe does not enter the disc, but rather is placed adjacent the outside of the disc. In this condition, the diagnostic element identifies a pathology on the outside surface of the disc, and the therapeutic element treats at least the outside surface of the disc. In preferred embodiments involving external treatment of the disc, the diagnostic element is an optical element, and the therapeutic element comprises an ultrasound transducer. In some embodiments, placing the probe adjacent the disc involves navigation around the outside of the disc. In some embodiments involving external treatment, therapeutic treatment produces disc shrinkage at a point of disc herniation where the herniation is identified externally by the diagnostic element and treated with the therapeutic element.

The outside posterior portion of the annulus fibrosus may have adhesions where the spinal cord outer membrane (dura) adheres to the annulus. Therefore, in some embodiments, the externally-based probe identifies and therapeutically treats (preferably by severing) these adhesions. The externally-based probe may also identify the location of certain structures (such as blood vessels or basivertebral nerves) that enter the vertebral body and which may be associated with pain. The identified structures could be therapeutically treated (by, for example, ablation).

In some embodiments, the probe enters the disc. In some embodiments thereof, the probe advances only into the annulus fibrosus. In other embodiments, the probe advances through the annulus fibrosus and into the nucleus pulposus. In some embodiments thereof, the therapeutic element treats the nucleus pulposus. In other embodiments, the therapeutic element treats the inner wall of the annulus fibrosus. In preferred embodiments involving advancing the probe into the nucleus pulposus, the diagnostic element is an optical element, and the therapeutic element delivers energy, preferably RF energy via an active electrode.

In some embodiments, a first probe can be used to deliver the diagnostic element to the disc, and a second probe can be used to deliver the therapeutic element to the disc. In preferred embodiments, each element is provided on the same probe. Providing both elements on the same probe is advantageous because only one breach in tissue need be made.

In some embodiments, the diagnostic and therapeutic probes are located at the distal end portion of the probe. Preferably, they are located so that the clinician can see the pathologic region through the diagnostic element while simultaneous treating the pathologic region with the therapeutic element. This provides the ability to provide real time, iterative treatment.

In preferred embodiments, the probe is navigable. Navigation may be accomplished by providing either a pre-bent or a bendable catheter. By moving the probe around the disc, the clinician can localize the zones where the pathologic region resides and then activate the therapeutic element to provide therapeutic treatment.

Smart navigation may be accomplished by using the diagnostic element (such as an optical diagnostic element such as a micro-endoscope) to guide the probe as it makes its way through the degenerative disc. Accordingly, in preferred embodiments, the optical element provides both visualization for guiding the probe through the target tissue and for diagnosing the pathologic region within the disc. Smart navigation provides a significant advantage over conventional intradiscal probes such as those disclosed by Sharkey that simply have a passive bend and are pushed around the nucleus pulposus by the clinician.

In preferred emboidment, the probe comprises an extruded tube having a dual lumen structure that houses a diagnostic element (such as an endoscope which has light and a video camera) in a first channel and a therapeutic element in a second channel.

In some embodiments, both the diagnostic and therapeutic elements advance and/or rotate in unison. In other embodiments, both the diagnostic and therapeutic elements are independently advanceable and/or rotateable within the probe.

The diagnostic element of the present invention includes any sensor that can record information on the state of the disc or disc component and transmit that information to the clinician. In preferred embodiments, the diagnostic element comprises a sensor for the measurement of a tissue property (such as fluorescence). In some embodiments, the diagnostic element comprises a sensor for the measurement of a function (such as electrical resistance, temperature or mechanical strength). In many embodiments, the sensor is typically a passive fiber (such as an optical fiber) through which energy (such as a spectrum of light) reflected or emitted from the target tissue is received by the sensor. In many embodiments, the energy received by the sensor is transmitted as a signal to a computer system and a display.

In some preferred embodiments, the diagnostic element further comprises an active element. The active element transmits energy to the target tissue so that the sensor can record the tissue response thereto. In many embodiments, the active element is an active fiber (such as an optical fiber) through which energy (such as a spectrum of light) is transmitted from a power source onto the target tissue.

Accordingly, in many embodiments, the diagnostic element comprises an active fiber adapted for transmitting energy (preferably, a spectrum of light) to the target tissue and a passive fiber for adapted for receiving energy (preferably, a spectrum of light) transmitted by or reflected from the target tissue.

In some embodiments, the diagnostic element is adapted to utilize an analytical technique selected from the group consisting of Raman spectroscopy, fluorescence, autofluorescence, reflected light, impedance, MRI and ultrasound as a means for identifying or analyzing the pathologic region. In some embodiments, a combination of these analytic techniques is used.

In some embodiments, the diagnostic element is adapted to utilize Raman spectroscopy as a means for identifying or analyzing the pathologic region. Raman spectroscopy has the advantage of being able to directly diagnose chemical bonds and provides more detail about the cells themselves. However, it is very sensitive and more difficult to collect the signal due to its weak strength.

In some embodiments, the diagnostic element is adapted to utilize fluorescence as a means for identifying or analyzing the pathologic region. Fluorescence has the advantage of being an easy to measure signal, but one must add a fluorophore (i.e. labeled antibody) and is thus more difficult to do clinically.

In some fluorescence embodiments involving autofluorescent tissues, the diagnostic element is adapted to utilize fluorescence as a means for identifying or analyzing the pathologic region. Autofluorescence has the advantage of not needing a contrast agent since it views endogenous (native) contrast. Autofluorescence is typically used for distinguishing malignant from nonmalignant tissue.

In some embodiments, the diagnostic element is adapted to utilize reflected light as a means for identifying or analyzing the pathologic region. Reflected light has the advantage of being the most simple light-based diagnostic technique, like vision. A bulk signal is detected when light is directed towards tissue. Since this technique has low sensitivity, it is advantageously combined with other diagnostic methods.

In some embodiments, the diagnostic element is adapted to utilize optical coherence tomography as a means for identifying or analyzing the pathologic region. Optical coherence tomography (OCT) has the advantage of seeing below the surface and getting information at depth. However, it requires long collection times and diagnoses a very small volume.

In some embodiments, the diagnostic element is adapted to utilize polarization as a means for identifying or analyzing the pathologic region. Polarization has the advantage of being a simple technique that senses contrast, has a large field of view, and may pick up subsurface phenomena. However, it is typically less specific than some of the other techniques (i.e. fluorescence).

In some embodiments, the diagnostic element comprises a plurality of sensors adapted to contact tissue and measure impedance over a range of frequencies from 10 kHz to 1 MHz in order to differentiate between normal and pathologic tissue.

In some embodiments, the diagnostic element comprises a coil adapted to act as a source for MRI and help resolve in the near field.

In some embodiments, the diagnostic element comprises a diagnostic ultrasound transducer for viewing the near field and differentiating between pathologic and normal tissue in the annulus.

In some embodiments, a second diagnostic element is also used. Preferably, the combination of diagnostic elements is located on the same probe. Preferably, the diagnostic element is adapted to utilize a combination of reflected light and autofluoescence as means for identifying or analyzing the pathologic region. The reflected light element is preferably used for smart navigation while the autofluoroscence element is used for diagnosis.

In some embodiments, the diagnostic element further comprises a computer having a data base of tissue properties. The computer is adapted to perform analysis of the information received from the passive sensor by comparing that information against a comparable tissue property information in its data base.

In some embodiments, the data base comprises information on tissue properties of normal and pathologic tissue, and the computer includes software for distinguishing normal tissue from pathologic tissue. In some embodiments, the data base comprises information on different types of tissue, and the computer includes software for identifying different types of tissue. In some embodiments, the data base comprises information on properties of treated tissue, and the computer comprises software for identifying treated tissue In some embodiments, the apparatus further comprises a feedback mechanism for insuring that the targeted pathologic tissue has been sufficiently treated. In some embodiments, the feedback mechanism is based upon the extent of blood flow.

Therefore, in accordance with the present invention, there is provided an apparatus for treating an intervertebral disc having a pathologic region, comprising:

a) a probe adapted to be positioned in or adjacent to a spinal disc, the probe comprising a diagnostic element comprising a sensor adapted to receive a signal from a target tissue and transmit the signal, and
b) a computer adapted to receive and analyze the signal transmitted by the sensor, the computer further comprising a data base.

In some embodiments, the diagnostic element provides information to a display located outside the patient. For example, in one preferred combination, a probe having an optical element enters the disc and records the condition of the inner wall of the annulus fibrosus. This information is then transmitted through a cable to a video monitor located in the same room as the patient, and the video monitor displays picture of the site recorded by the optical probe. The clinician can then view the monitor and identify when the optical probe has identified a pathologic region.

Generally, the therapeutic element of the present invention includes any element that can provide a local therapeutic treatment to the disc. In some embodiments, the therapeutic element is selected from the group consisting of:

(a) an element capable of delivering energy to tissue in a therapeutic amount (such as a thermal energy delivery device),
(b) an element capable of delivering or removing a material from a location adjacent the element's location in the probe (such as an opening in the catheter for delivery of a fluid or for suction);
(c) a mechanical grasping tool for removing or depositing a solid (such as a cutting tool, which includes all similar operations, such as puncturing); and
(d) a guidance tool for allowing passage of other devices (such as a catheter), or
(e) a functional element having a combination of these elements.

In some preferred embodiments, the therapeutic element is an energy delivery element. Preferably, the energy delivery element is selected from the group consisting of a laser, an ultrasound element comprising a therapeutic ultrasound transducer, a microwave element, a RF energy element, and an ohmic heating element. More preferably, the RF energy element comprises an active element and a return electrode. More preferably, the active and return electrodes are disposed on the same probe.

In some embodiments, the therapeutic element may include a portion of the probe. For example, in the case of an electrically conductive probe having insulated portion and a non-insulated portion in electrical connection with a power supply, the uninsulated portion of the probe could be considered to be an electrode, and so would be considered to be a therapeutic element.

In some embodiments, the probe comprises a plurality of therapeutic elements. Preferably, the therapeutic element are spaced from each other to define a plurality of zones of activation. These zones may defined by either axial or radial spacing of the therapeutic elements. In use, the clinician may use the diagnostic element to identify a pathologic region requiring treatment and then select the therapeutic element in the zone closest to the pathology. The therapeutic element is then activated to treat the pathology without moving the treatment device.

Alternatively, the plurality of therapeutic elements comprises different types of therapeutic elements (such as one RF energy element and one ultrasound element). In use, the clinician may use the diagnostic element to identify a pathologic region requiring treatment and then select the therapeutic element within the plurality most capable of providing the most appropriate type of treatment (e.g., ablation or shrinkage). In some preferred embodiments, the combination comprises a diagnostic element (more preferably, an optical diagnostic element) and an energy delivery element. In some embodiments, the diagnostic element is located distal to the therapeutic element.

Figure 2:
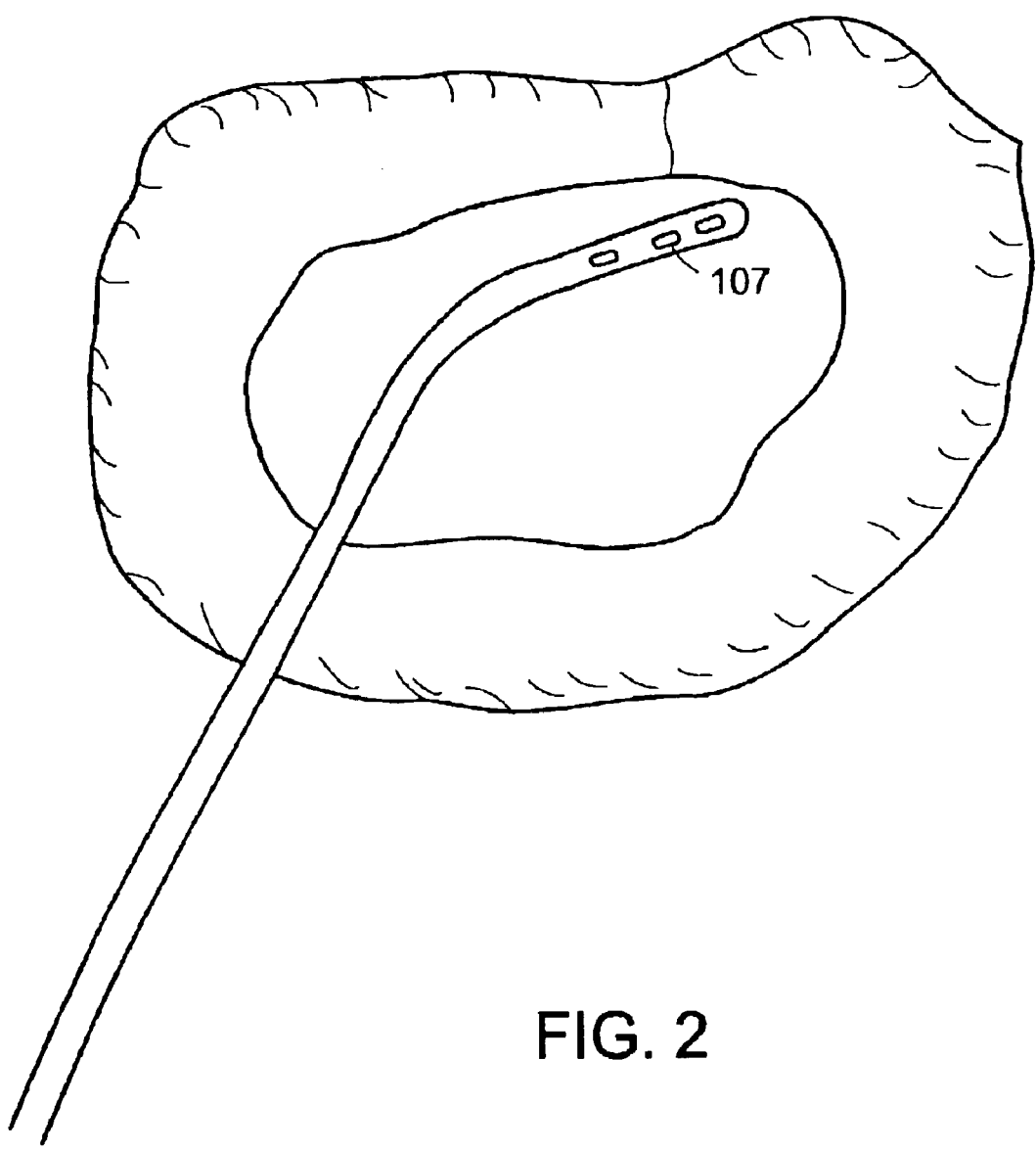

Now referring to FIGS. 1 and 2, there is provided a preferred probe 101 of the present invention located within the nucleus pulposus 203 of an intervertebral disc 201. The probe has a proximal end 103 configured to connect to a power source so that the probe can receive and transmit diagnostic signals and transmit therapy. The distal end 105 of the probe contains first 107 and second 109 therapeutic elements (preferably, thermal effectors adapted to provide thermal therapy to the pathologic region), and an diagnostic element 111 (preferably, an optical element) adapted to receive and transmit diagnostic signals. In this case, the diagnostic element is located distal to the therapeutic elements. In use, as in FIG. 1, the diagnostic element identifies a pathologic region (such as a fissure 205) located on the inner wall 207 of the annulus fibrosus. Once the pathologic region is identified, now referring to FIG. 2, the probe is moved through smart navigation to the pathologic region so that therapeutic element 107 is closely adjacent the pathologic region. The therapeutic element is then activated and provides therapy to the pathologic region.

Figure 3:
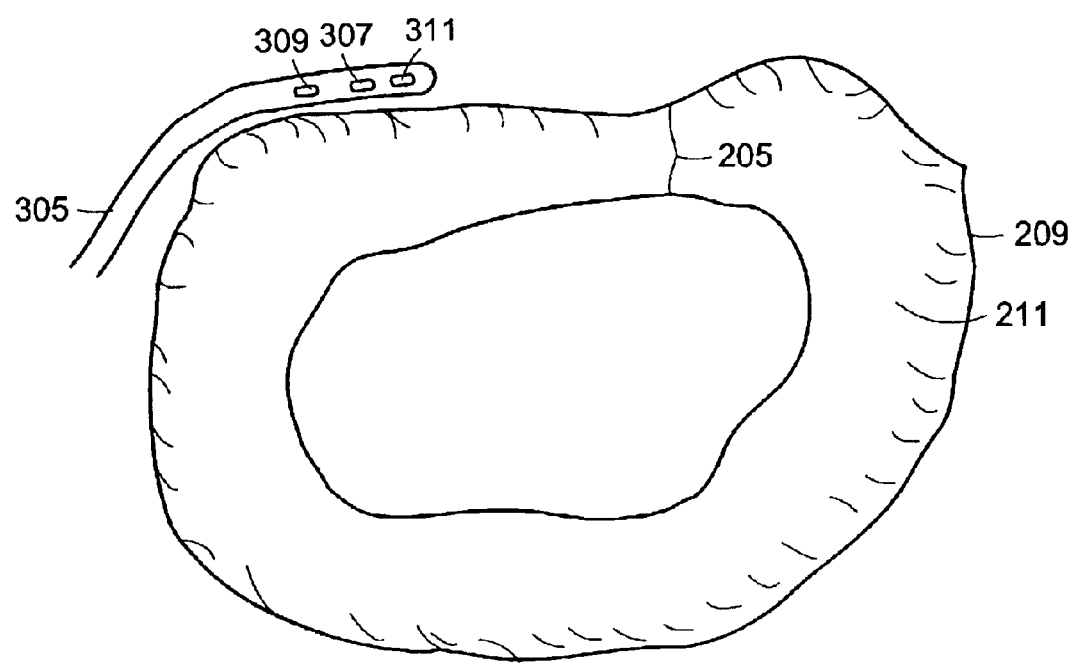
FIGS. 3 and 4 disclose a preferred probe of the present invention adjacent the outer wall of an intervertebral disc.
Figure 4:
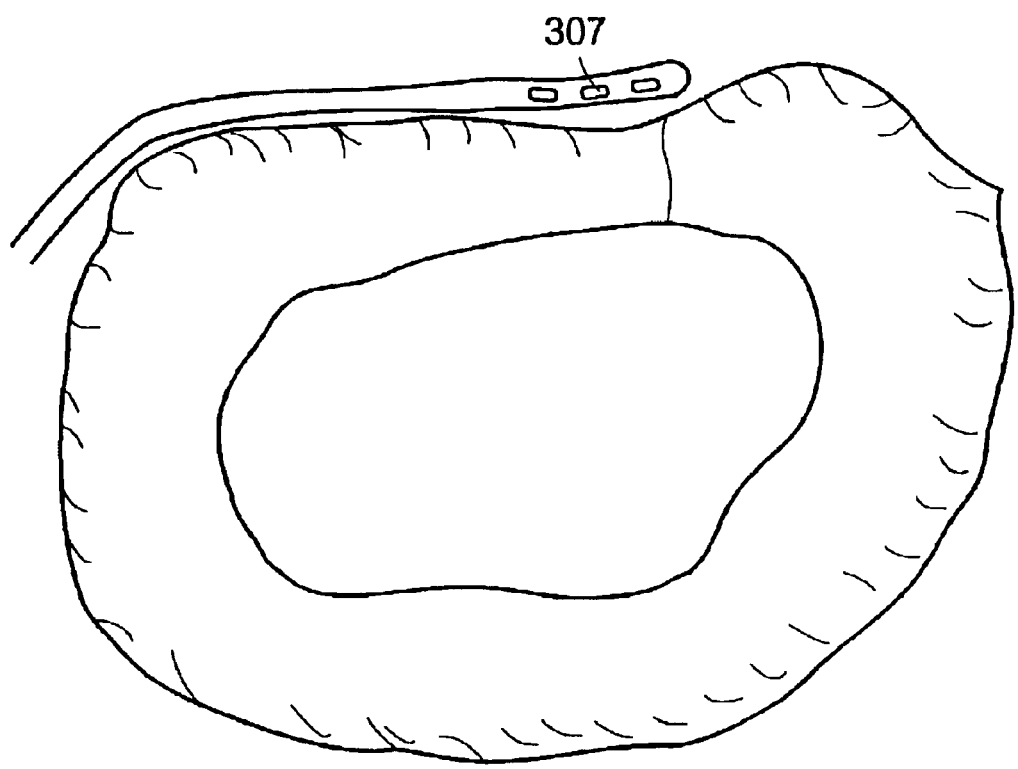

Now referring to FIGS. 3 and 4, there is provided a preferred probe 301 of the present invention located on the outer wall 209 of the annulus fibrosus 211 of an intervertebral disc 201. The distal end 305 of the probe contains first 307 and second 309 therapeutic elements (preferably, ultrasound transducers adapted to provide thermal therapy to the pathologic region), and an diagnostic element 311 (preferably, an optical element) adapted to receive and transmit diagnostic signals. Again, the diagnostic element is located distal to the therapeutic elements. In use, as in FIG. 3, the diagnostic element identifies a pathologic region (such as a fissure 205) located on the outer wall 209 of the annulus fibrosus. Once the pathologic region is identified, now referring to FIG. 4, the probe is moved through smart navigation to the pathologic region so that therapeutic element 307 is closely adjacent the pathologic region. The therapeutic element is then activated and provides therapy to the pathologic region.

Therefore, in accordance with the present invention, there is provided a method of therapeutically treating an intervertebral disc having a pathologic region, the method comprising the steps of:

a) navigating a probe having a diagnostic element and a therapeutic element to a first position within or adjacent to the disc,
b) activating the diagnostic element to identify the pathologic region within the disc,
c) navigating the probe to a second position closer to the pathologic region identified in step b), and
d) activating the therapeutic element to treat the pathologic region.

Figure 5:
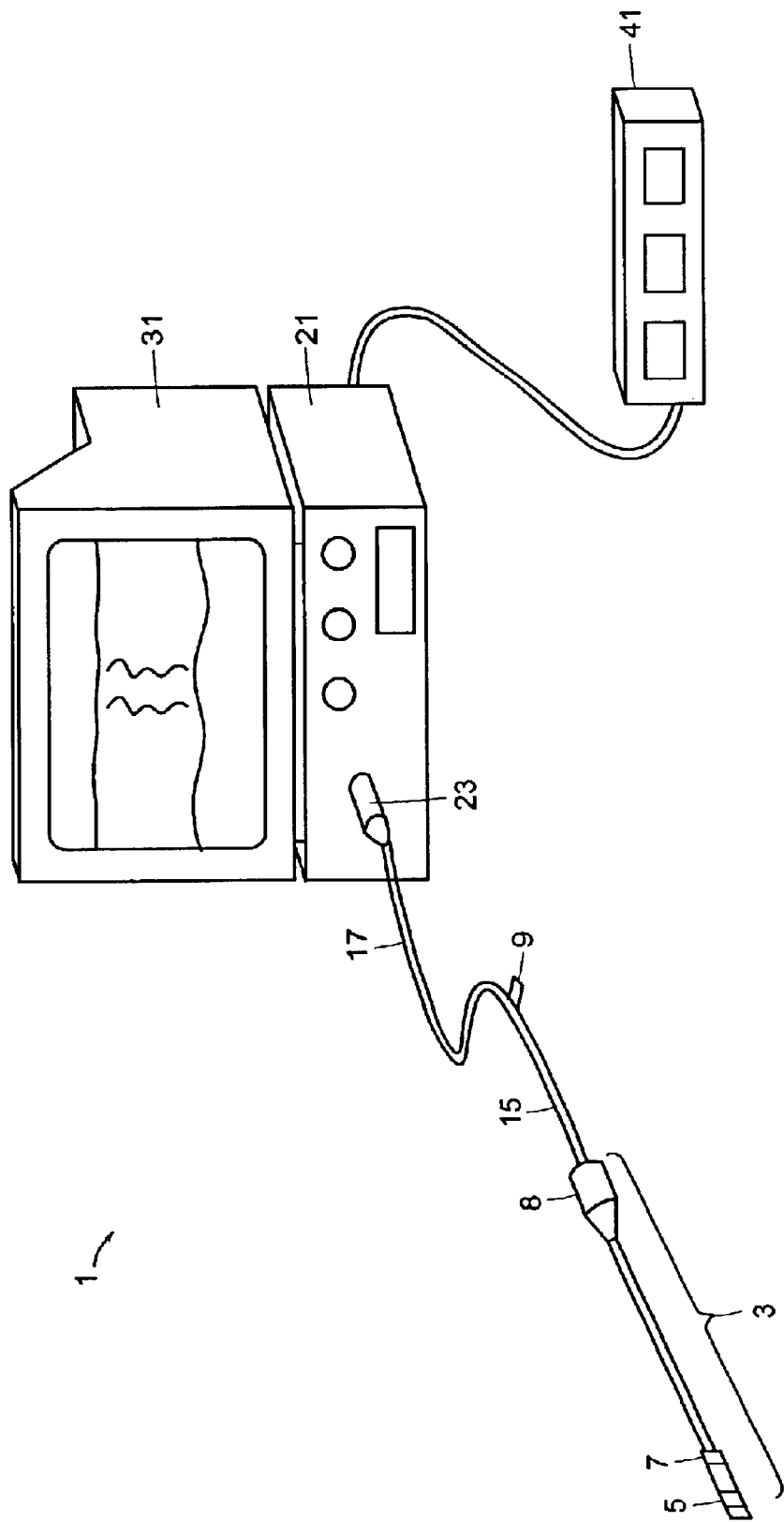
FIG. 5 describes a preferred apparatus for use in the present invention.

Now referring to FIG. 5, there is provided a preferred apparatus 1 for treating spinal pathologies, comprising:
a) a combined diagnostic and therapeutic probe 3 having a diagnostic element 5 and a therapeutic element 7, and a proximal end 8, b) a first cable 9 having a diagnostic signal conduit (not shown) and a therapy delivery conduit (not shown), and first 15 and second 17 ends, the first end of the cable being attached to the proximal end of the probe, c) a power source 21 having i) an input/output port 23 adapted to provide therapeutic energy to the probe, and to receive and transmit diagnostic signals from and to the probe, the port being attached to the second end of the first cable, d) a video monitor 31 connected to the signal output port adapted to display the diagnostic signals, e) a foot control 41 in electrical connection with the power source and adapted to allow the clinician to control the power source.

EXAMPLE

This prophetic example describes one preferred "see and treat" procedure for treating an intervertebral disc.

In a prophetic example, the patient lies on the table in a prone position (face down). The patient's back is scrubbed with an iodine solution and under fluoroscopic guidance, and a hollow 16-11 gage needle with stylet is placed for localization. The appropriate disc level is checked and verified. At an appropriate angle of entry, the needle is advanced into the disc. The needle is placed through the annulus fibrosis and just penetrates the nucleus pulposis and the stylet is removed. The probe of the present invention is then placed into the nucleus pulposus through the guide needle.

Once the probe has been inserted into the nucleus pulposus, the clinician preferably follows the following procedure:

a) navigate the probe to a first position within or adjacent to the target tissue, b) activate the diagnostic element to identify the pathologic region within the target tissue, c) navigate the probe to a second position closer to the pathologic region identified in step b), d) activate the therapeutic element to treat the pathologic regoin, and e) activate the diagnostic element to confirm the therapeutic treatment of the pathologic tissue.

In some embodiments, second and third successive target sites will be sought out, identified and treated.

In some embodiments, the probe comprises a plurality of diagnostic elements (preferably at least five covering a distance along the probe of 25 mm) and a plurality of therapeutic elements (preferably at least five covering a distance along the probe of 25 mm) wherein the sequence of diagnostic elements and therapeutic elements alternates along the probe. In use, using external fluoroscopic guidance, this probe is placed in a final position in the disc along the posterior wall of the disc. The diagnostic elements are then activated to identify the pathologic region and the therapeutic element closest to the identified pathologic region is activated to treat the pathologic region. In other embodiments, more than one of the therapeutic elements of this probe is activated.

We claim:

1. A method of therapeutically treating an intervertebral disc having a pathologic region, the method comprising the steps of:

a) positioning a probe having a diagnostic element adjacent to the disc, b) activating the diagnostic element to identify the pathologic region as the probe is adjacent the disc, and c) therapeutically treating the identified pathologic region.

2. The method of claim 1 wherein the treatment comprises coagulating a collagen component of an annulus fibrosus portion of the disc.

3. The method of claim 1 wherein the treatment comprises denervating a nociceptor contained within an annulus fibrosus portion of the disc.

4. The method of claim 1 wherein the probe is positioned via a percutaneously placed needle.

5. The method of claim 1 wherein the probe further comprises a therapeutic element, and the therapeutic element carries out the treatment step.

6. The method of claim 5 wherein the diagnostic element comprises an optical sensor and the therapeutic element comprises an ultrasound transducer.

7. The method of claim 1 wherein the pathologic region is on an outside surface of the disc, and the treatment treats at least the outside surface of the disc.

8. The method of claim 7 wherein the therapeutic treatment produces disc shrinkage at a point of disc herniation.

9. The method of claim 7 wherein the pathologic region comprises adhesions located on an outside posterior portion of the disc where a spinal cord outer membrane adheres to an annulus fibrosus.

10. The method of claim 7 further comprising the steps of:

d) identifying a location of a structure of an adjacent vertebral body, and e) therapeutically treating the identified structure.

11. The method of claim 1 wherein the probe further comprises a therapeutic element and the therapeutic element treats an inner wall of the annulus fibrosus.

12. The method of claim 1 wherein the probe further comprises a therapeutic element, the diagnostic element is an optical element, and the therapeutic element delivers energy via an active electrode.

13. The method of claim 1 wherein the probe further comprises a therapeutic element.

14. The method of claim 1 wherein the diagnostic element is adapted to utilize an analytical technique selected from the group consisting of Raman spectroscopy, fluorescence, autofluorescence, reflected light, impedance, MRI and ultrasound as a means for identifying or analyzing the pathologic region.

15. The method of claim 14 wherein the probe comprises at least two different diagnostic elements.

16. The method of claim 15 wherein the two different diagnostic elements are adapted to respectively utilize the analytic techniques of reflected light and autofluoroscence.

17. The method of claim 1 wherein the probe further comprises a therapeutic element selected from the group consisting of:

i) an element capable of delivering energy to tissue in a therapeutic amount, ii) an element capable of delivering or removing a material from a location adjacent the element's location in the probe;

iii) a mechanical grasping tool for removing or depositing a solid; and iv) a guidance tool for allowing passage of other devices.

18. The method of claim 17 wherein the therapeutic element is an energy delivery element.

19. The method of claim 18 wherein the energy delivery element is selected from the group consisting of a laser, a ultrasound element comprising an ultrasound transducer, a microwave element, and an RF energy element.

20. The method of claim 18 wherein the therapeutic element is an RF energy element comprising an active electrode and a return electrode.

21. The method of claim 20 wherein the active and return electrodes are disposed on the same probe.

22. The method of claim 1 wherein the step of activating the diagnostic element to identify the pathologic region comprises the substep of performing analysis of information received from a passive sensor by comparing the information against a comparable tissue property information in a computer data base.

23. A method of therapeutically treating an intervertebral disc having a pathologic region, the method comprising the steps of:
   a) navigating a probe having a diagnostic element and a therapeutic element to a first position adjacent to the disc,
   b) activating the diagnostic element to identify the pathologic region within the disc as the probe is adjacent the disc,
   c) navigating the probe to a second position closer to the pathologic region identified in step b), and
   d) activating the therapeutic element to treat the pathologic region.

24. The method of claim 23 further comprising the step of:
   d) activating the diagnostic element to confirm the therapeutic treatment of the pathologic tissue.

25. A method of therapeutically treating an intervertebral disc having a pathologic region, the method comprising the steps of:
   a) positioning a probe having a diagnostic element and a therapeutic element adjacent to the disc, the diagnostic element comprising a sensor and an active element,
   b) transmitting energy through the active element to target tissue to produce a signal from the pathologic region as the probe is adjacent the disc,
   c) transmitting the signal through the sensor,
   d) evaluating the signal to identify the pathologic region, and
   e) therapeutically treating the identified pathologic region.

26. The method of claim 25 wherein the therapeutic element of the probe performs step e).

* * * * *